United States Patent [19]

Lin

[11] 4,436,837

[45] Mar. 13, 1984

[54] PREPARATION OF ALKANOLS FROM SYNTHESIS GAS

[75] Inventor: Jiang-Jen Lin, Round Rock, Tex.

[73] Assignee: Texaco Inc., White Plains, N.Y.

[21] Appl. No.: 428,491

[22] Filed: Sep. 29, 1982

[51] Int. Cl.³ .............................................. C07C 27/06
[52] U.S. Cl. ...................................... 518/700; 502/164
[58] Field of Search ......................................... 518/700

[56] References Cited

U.S. PATENT DOCUMENTS 4,362,821 12/1982 Lin ....................................... 518/700

Primary Examiner—Howard T. Mars
Attorney, Agent, or Firm—Robert A. Kulason; Jack H. Park; Richard A. Morgan

[57] ABSTRACT

This invention concerns a process for making alkanols and esters which comprises reacting a mixture of CO and $H_2$ at a pressure of about 500 psig or greater and at a temperature of at least 150° C. in the presence of a catalyst system comprising a ruthenium-containing compound, a samarium compound and a quaternary phosphonium salt, in the presence of an inert, oxygenated solvent.

18 Claims, No Drawings

PREPARATION OF ALKANOLS FROM SYNTHESIS GAS

BACKGROUND OF THE INVENTION

1. Field of the Invention

This invention concerns an improved process for preparing alkanols and esters by reaction of oxides of carbon with hydrogen in presence of a catalyst system.

2. Prior Art

It has long been known that monofunctional alcohols such as methanol, ethanol, etc. can be formed by the reaction of synthesis gas, i.e., a mixture of carbon monoxide and hydrogen at elevated pressures of, for example, up to 1000 atmospheres, and at temperatures of from about 200° to 500° C., or more using a mixture of copper, chromium and zinc oxides as catalyst. A wide variety of other catalyts have been employed in the reaction of carbon monoxide and hydrogen to yield liquid products containing substantial amounts of monofunctional alcohols as exemplified by methanol, ethanol, propanol, etc. For example, in U.S. Pat. No. 4,013,700 the reaction of carbon monoxide and hydrogen in the presence of a quaternary phosphonium cation and a rhodium carbonyl complex yields a liquid product having a high methanol content. In U.S. Pat. No. 4,014,913 where the same reactants are contacted with a solid catalyst comprising a combination of rhodium and manganese the product formed contains substantial amounts of ethanol and in U.S. Pat. No. 4,197,253 where the reaction of carbon monoxide and hydrogen is conducted in the presence of a rhodium carbonyl complex and a phosphine oxide compound the resulting product contains a high concentration of methanol. Likewise, when the same reactants are contacted with a rhodium carbonyl complex and a copper salt a liquid product containing a substantial amount of methanol is formed. In U.S. Pat. Nos. 4,332,914 and 4,332,915 where the reaction of carbon monoxide and hydrogen is conducted with a ruthenium catalyst and a cobalt, rhenium or manganese co-catalyst dispersed in a low melting quaternary phosphonium salt, a wide spectrum of alkanol and ester products were produced.

One serious problem associated with synthesis gas operations in the past has been the non-selectivity of the product distribution since high activity catalysts generally yield a liquid product containing numerous hydrocarbon materials. Thus, complicated recovery schemes are necessary to separate the desired products and the overall yield of the valuable organic products is low. There is a definite need in the art for a process which will produce alkanols and especially ethanol rich alkanols with a high degree of selectivity from synthesis gas.

This invention therefore is to provide a process of making alkanols by resort to a unique catalyst system which produces said alkanols in good yields and with excellent selectivity especially with regard to ethanol and methanol formation.

SUMMARY OF THE INVENTION

This invention concerns a method for making alkanols and esters which comprises reacting a mixture of CO and $H_2$ at a pressure of about 500 psig or greater and at a temperature of at least 150° C. in the presence of a catalyst system comprising a ruthenium-containing compound, a samarium-containing compound and a quaternary phosphonium salt, in the presence of an inert, oxygenated solvent.

DETAILED DESCRIPTION OF THE INVENTION

In the narrower and more preferred practice of this invention alkanols and esters are prepared by reacting a mixture of CO and $H_2$ at a temperature of about 180° to about 250° C. and at a pressure of 2000 psig or greater in the presence of a catalyst system comprising one or more ruthenium-containing compounds, one or more samarium-containing compounds and a quaternary phosphonium salt and in the presence of an inert, oxygenated solvent such as 1,4-dioxane.

As previously pointed out, the catalyst system employed in the practice of this invention contains one or more ruthenium-containing compounds and one or more samarium-containing compounds together with a quaternary phosphonium salt. The ruthenium-containing catalyst as well as the samarium-containing catalyst may be chosen from a wide variety of organic or inorganic compounds, complexes, etc., as will be shown and illustrated below. It is only necessary that the catalyst precursor actually employed contain the said metals in any of their ionic states. The actual catalytically active species is then believed to comprise ruthenium and samarium in complex combination with, for example, tetraalkylphosphonium bromide as well as carbon monoxide and hydrogen.

The ruthenium catalyst precursors may take many different forms. For instance, the ruthenium may be added to the reaction mixture in an oxide form, as in the case of for example, ruthenium(IV) oxide hydrate, anhydrous ruthenium(IV) dioxide and ruthenium(VIII) tetraoxide. Alternatively, it may be added as the salt of a mineral acid, as in the case of ruthenium(III) chloride hydrate, ruthenium(III) bromide, ruthenium(III) iodide, tricarbonyl ruthenium(II) iodide, anhydrous ruthenium-(III) chloride and ruthenium nitrate, or as the salt of a suitable organic carboxylic acid, for example, ruthenium(III) acetate, ruthenium naphthenate, ruthenium valerate and ruthenium complexes with carbonyl-containing ligands, such as ruthenium(III) acetylacetonate. The ruthenium may also be added to the reaction zone as a carbonyl or hydrocarbonyl derivative. Here, suitable examples include triruthenium dodecacarbonyl and other hydrocarbonyls such as $H_2Ru_4(CO)_{13}$ and $H_4Ru_4(CO)_{12}$, and substituted carbonyl species such as the tricarbonylruthenium(II) chloride dimer, $[Ru(CO)_3Cl_2]_2$.

Preferred ruthenium-containing compounds include oxides of ruthenium, ruthenium salts of an organic carboxylic acid and ruthenium carbonyl or hydrocarbonyl derivatives. Among these, particularly preferred are ruthenium dioxide hydrate, ruthenium tetraoxide, anhydrous ruthenium(IV) oxide, ruthenium acetate, ruthenium(III) acetylacetonate, and triruthenium dodecacarbonyl.

The samarium compound is one of the lanthanides series, in which the 4f electron orbitals are available for coordinating with other metals or ligands. The samarium catalyst precursors may take many different forms. For instance, the samarium may be added in an oxide form, as in the case of, for example, samarium oxide. Alternatively, they may be added as salts of a mineral acid, as in the case of samarium chloride, samarium bromide, samarium fluoride, samarium sulfate and samarium nitrate. Samarium carbide, carbonyl, hydrocarbonyl, boride and carboxylates, such as samarium hydride, samarium oxalate and samarium acetate are also effective catalyst precursors.

Quaternary phosphonium salts suitable for use in this invention have the formula:

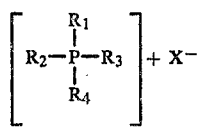

where $R_1$, $R_2$, $R_3$ and $R_4$ are organic radicals, particularly aryl or alkaryl radicals bonded to the phosphorous atom, and X is an anionic species. The organic radicals useful in this instance include those alkyl radicals having 1 to 20 carbon atoms in a branched or linear alkyl chain; they include the methyl, ethyl, n-butyl, iso-butyl, octyl, 2-ethylhexyl and dodecyl radicals. Tetraethylphosphonium bromide and tetrabutylphosphonium bromide are typical examples presently in commercial production. The corresponding quaternary phosphonium acetates, nitrates, chromates, tetrafluoroborates and other halides, such as the corresponding chlorides, and iodides, are also satisfactory in this instance.

Equally useful are the phosphonium salts containing phosphorus bonded to a mixture of alkyl, aryl and alkaryl radicals. Said aryl and alkaryl radicals may each contain 6 to 20 carbon atoms. The aryl radical is most commonly phenyl. The alkaryl group may comprise phenyl substituted with one or more $C_1$-$C_{10}$ alkyl substituents, bonded to the phosphorus atom through the aryl function.

Illustrative examples of suitable quaternary phosphonium salts include tetrabutylphosphonium bromide, heptyltriphenylphosphonium bromide, tetrabutylphosphonium iodide, tetrabutylphosphonium chloride, tetrabutylphosphonium nitrate, tetrabutylphosphonium chromate, tetrabutylphosphonium tetrafluoroborate and tetrabutylphosphonium acetate.

The preferred quaternary salts are generally the tetralkylphosphonium salts containing alkyl groups having 1-6 carbon atoms, such as methyl, ethyl, and butyl.

Preferred tetrabutylphosphonium salts include the bromide, chloride, iodide, acetate and chromate salts. Tetrabutylphosphonium salts, such as tetrabutylphosphonium bromide, are most preferred for the practice of this invention. Mixtures of these quaternary salts may also be employed, if desired.

Generally, in the catalyst system the molar ratio of the ruthenium compound to the quaternary phosphonium salt will range from about 1:0.01 to about 1:100 or more and, preferably, will be from about 1:1 to about 1:20.

The quantity of ruthenium compound and the samarium-containing compound employed in the instant invention may vary over a wide range. In general, the novel process is desirably conducted in the presence of a catalytically effective quantity of the active ruthenium species and of the samarium species which gives the desired product in reasonable yield. The reaction proceeds when employing as little as about $1 \times 10^{-6}$ weight percent, and even lesser amounts, of ruthenium together with about $1 \times 10^{-6}$ weight percent or less of samarium basis the total weight of the reaction mixture. The upper concentration is dictated by a variety of factors including catalyst cost, partial pressures of carbon monoxide and hydrogen, operating temperature, etc. A ruthenium concentration of from about $1 \times 10^{-3}$ to about 10 weight percent in conjunction with a samarium concentration of from about $1 \times 10^{-3}$ to about 10 weight percent, based on the total weight of reaction mixture is generally desirable in the practice of this invention. The preferred ruthenium-to-samarium atomic ratio is from about 10:1 to about 0.1:1. Mixtures of the samarium-containing compounds may be employed in the catalyst system, if desired.

The choice of a suitable solvent can be important when a large scale, continuous phase reactor is used. A homogeneous solution must be obtained so that the continuous feeding of catalyst is feasible. The solvents useful in the process of this invention are oxygenated hydrocarbons i.e., compounds composed of carbon, hydrogen and oxygen in which the only oxygen atoms present are in ether group, ester groups, ketone group or hydroxyl groups of alcohols. Generally, the oxygenated hydrocarbon will contain 3 to 12 carbon atoms. The solvent must be substantially inert under reaction conditions and it must be one which has a normal boiling point of at least 40° C. at atmospheric pressure and preferably, the solvent will have a boiling point greater than that of ethanol and other oxygen-containing reaction products so that recovery of the solvent by distillation is facilitated.

Preferred ester-type solvents are the aliphatic and acylic carboxylic acid monoesters as exemplified by butyl acetate, methyl benzoate, isopropyl iso-butyrate and propyl propionate as well as dimethyl adipate. Useful alcohol-type solvents include monohydric alcohols such as cyclohexanol, 1-hexanol, neopentanol, 2-octanol, etc. Suitable ketone-type solvents include, for example, cyclic ketones, such as cyclohexanone and 2-methylcyclohexanone, as well as acyclic ketones such as 2-pentanone, butanone, acetophenone, etc. Ethers which may be utilized as solvents include cyclic, acyclic and heterocyclic materials. Preferred ethers are the heterocyclic ethers as illustrated by 1,4-dioxane and 1,3-dioxane. Other suitable ether solvents include di-n-propyl ether, diethylene glycol dibutyl ether, dibutyl ether, ethyl butyl ether, diphenyl ether, heptyl phenyl ether, anisole, tetrahydrofuran, etc. The most useful solvents of all of the above group include the ethers as represented by monocyclic, heterocyclic ethers such as 1,4-dioxane, etc.

The temperature range which can usefully be employed in these syntheses is a variable dependent upon other experimental factors, including the pressure, and the concentration and choice of the particular species of ruthenium and samarium catalysts among other things. The range of operability is from about 150° C. to 350° C. when superatmospheric pressures of synthesis gas are employed. A narrow range of 180° to 250° C. represents the preferred temperature range.

Superatmospheric pressures of about 500 psi or greater lead to substantial yields of alkanols by the process of this invention. A preferred operating range is from 2000 psi to 8000 psi, although pressures above 8000 psi also provide useful yields of the desired alkanols.

The relative amounts of carbon monoxide and hydrogen which may be initially present in the syngas, i.e., synthesis gas mixture are variable, and these amounts may be varied over a wide range. In general, the mole ratio of $CO:H_2$ is in the range from about 20:1 up to about 1:20, preferably from about 5:1 to 1:5, although ratios outside these ranges may also be employed. Particularly in continuous operations, but also in batch experiments, the carbon monoxide-hydrogen gaseous mixtures may also be used in conjunction with up to 50 percent by volume of one or more other gases. These other gases may include one or more inert gases such as nitrogen, argon, neon and the like, or they may include gases that may, or may not, undergo reaction under CO hydrogenation conditions, such as carbon dioxide, hydrocarbons such as methane, ethane, propane and the like, ethers such as dimethyl ether, methylethyl ether and diethyl ether, alkanols such as methanol and acid esters such as methyl acetate.

Esters of monocarboxylic acids may also be formed during the course of this alkanol synthesis. Most often these are ester derivatives of acetic acid such as methyl acetate, ethyl acetate, etc. These esters and the individual alkanols formed which include, ethanol, propanol and butanol in addition to methanol can be conveniently recovered from the reaction mixture by distillation, extraction, etc.

The novel process of this invention can be conducted in a batch, semi-continuous or continuous fashion. The catalyst may be initially introduced into the reaction zone batchwise, or it may be continuously or intermittently introduced into such a zone during the course of the synthesis reaction. Operating conditions can be adjusted to optimize the formation of the desired alkanol product, and said material may be recovered by methods well known in the art, such as distillation, fractionation, extraction and the like. A fraction rich in the ruthenium and samarium catalyst components may then be recycled to the reaction zone, if desired, and additional products generated.

The products have been identified in this work by one or more of the following analytical procedures, viz, gas-liquid phase chromatograph (glc), infrared (ir), mass spectrometry, nuclear magnetic resonance (nmr) and elemental analyses, or a combination of these techniques. Analyses have, for the most part, been by parts in weight; all temperatures are in degrees centigrade and all pressures in pounds per square inch gauge (psig).

Various embodiments of the process of this invention are illustrated in the following examples which are to be considered not limitative.

Selectivity to individual aliphatic oxygenated products in the crude liquid product has been estimated in this work using the equation:

$$\text{Selectivity} = \left( \frac{X}{100 - S} \right) \times 100\%$$

where X=Wt% concentration of the individual product in the crude liquid product as determined by glc.

S=Wt% concentration of solvent in the crude liquid product as determined by glc.

The product weight gain was estimated, in grams, as the weight difference between the crude liquid product and the total solvent plus catalysts charged at the start of the run.

EXAMPLE 1

(Comparative)

This example illustrates a synthesis of a mixture of alkanols and esters where the reaction of carbon monoxide and hydrogen is catalyzed by ruthenium together with tetrabutylphosphonium bromide salt and where the reaction is conducted in the presence of 1,4-dioxane. There is no second metal involved in this comparative example.

In the examples which follow the effect on product selectivity will be observed with the use of a second transition metal catalyst.

In Example I a glass liner was charged with hydrated ruthenium oxide (0.19 g, 1.0 mmole), tetra-n-butylphosphonium bromide (3.4 g, 10 mmoles), and 1,4-dioxane (10 g). The glass liner was placed in a stainless steel reactor and purged of air with hydrogen and carbon monoxide (1:1 molar ratio), then pressured to 1000 psi, and heated to 220° C. The pressure was brought up to 6300 psi and during the reaction period the constant pressure was maintained by using a surge tank. After 18 hours the reactor was allowed to cool, the excess gas sampled and vented and the liquid products recovered.

The liquid products, which were obtained with an 8.5 g weight gain, were analyzed by glc and the following product selectivities (on solvent-free basis) were obtained:

| | |
|---|---|
| methanol | 43 Wt % |
| ethanol | 24 Wt % |
| n-propanol | 7 Wt % |
| n-butanol | 8 Wt % |
| methyl acetate | 3 Wt % |
| ethyl acetate | 3 Wt % |
| n-propyl acetate | 0 Wt % |

Catalyst productivity (based on weight gain)=8500 g/g-atm-Ru.

A typical off-gas analysis showed the presence of:

| | |
|---|---|
| carbon monoxide | 36 Wt % |
| hydrogen | 41 Wt % |
| carbon dioxide | 17 Wt % |
| methane | 3.4 Wt % |

The water content in liquid product (Karl-Fischer titration) was 0.75%. It is realized that methanol is the major component in the liquid product distribution and the ratio of methanol to ethanol is about 1.8:1.0 (43 Wt% vs 24 Wt %).

EXAMPLE II

This example illustrates a typical synthesis of a mixture of alkanols where the reaction of carbon monoxide and hydrogen is catalyzed by ruthenium together with a samarium-containing compound and tetrabutylphosphonium bromide and where the reaction is conducted in the presence of p-dioxane.

To a glass liner was charged hydrated ruthenium oxide (0.19 g, 1.0 mmole) tetra-n-butylphosphonium bromide (3.4 g, 10 mmoles), hydrated samarium chloride (0.090 g, 0.25 mmole) and 1,4-dioxane (10 g). The glass liner was placed in a stainless steel reactor and purged of air with hydrogen and carbon monoxide (1:1 molar ratio), then pressured to 2000 psi, and heated to 220° C. The pressure was brought up to 8000 psi and during the reaction period the constant pressure was maintained by using a surge tank. After 16 hours, the reactor was allowed to cool, the excess gas sampled and vented and the liquid products recovered.

The liquid products, which were obtained with a 9.5 g weight gain, were analyzed by glc and Karl Fischer titration and the following product selectivities were obtained:

| | |
|---|---|
| methanol | 29 Wt % |
| ethanol | 34 Wt % |
| n-propanol | 6 Wt % |
| n-butanol | 3 Wt % |
| methyl acetate | 11 Wt % |
| ethyl acetate | 7 Wt % |
| n-propyl acetate | 0 Wt % |
| water | 0.08 Wt % |

Catalyst productivity (based on weight gain)=9500 g/g-atm-Ru.

Typical off-gas samples from the same experiment showed the presence of:

| | |
|---|---|
| carbon monoxide | 24 Wt % |
| hydrogen | 33 Wt % |
| carbon dioxide | 32 Wt % |
| Methane | 7 Wt % |

It is realized that ethanol is the major component in the liquid product distribution and the ratio of methanol to ethanol is about 1.0:1.2 (29% vs 34%), which is significantly different from Example I.

EXAMPLE III

The experiment of Example II was repeated, except the syngas pressure was brought up to 6300 psi during the reaction period.

To a glass liner was charged hydrated ruthenium oxide (0.19 g, 1.0 mmole), tetra-n-butylphosphonium bromide (3.4 g, 10 mmoles), hydrated samarium chloride (0.090 g, 0.25 mmole) and 1,4-dioxane (10 g). The glass liner was placed in a stainless steel reactor and purged of air with hydrogen and carbon monoxide (1:1 molar ratio). Then pressured to 2000 psi and heated to 220° C. The pressure was brought up to 6300 psi and during the reaction period the constant pressure was maintained by using a surge tank. After 16 hours, the reactor was allowed to cool, the excess gas vented and the liquid products recovered.

The liquid products, which were obtained with a 6.6 g weight gain, were analyzed by glc and Karl Fischer titration and the following product selectivities were obtained:

| | |
|---|---|
| methanol | 30 Wt % |
| ethanol | 28 Wt % |
| n-propanol | 4 Wt % |
| n-butanol | 4 Wt % |
| methyl acetate | 11 Wt % |
| ethyl acetate | 8 Wt % |
| water | 0.75 Wt % |

Catalyst productivity (based on weight gain)=6600 g/g-atm-Ru. The ratio of methanol to ethanol in the liquid product, is about 1.07:1.0 (30 Wt.% vs 28 Wt.%).

EXAMPLE IV

The procedure of Example III was repeated, except the ratio of ruthenium to samarium was varied and the pressure used was 6000 psi.

To a glass liner was charged hydrated ruthenium oxide (0.19 g, 1.0 mm), tetra-n-butylphosphonium bromide (3.4 g, 10 mmoles), hydrated samarium chloride (0.36 g, 1.0 mmole) and 1,4-dioxane (10.0 g). The glass liner was placed in a stainless steel reactor and purged of air with hydrogen and carbon monoxide (1:1 molar ratio) then pressured to 2000 psi and heated to 220° C. The pressure was brought up to 6000 psi and during the reaction period the constant pressure was maintained by using a surge tank. After 16 hours, the reactor was allowed to cool, the excess gas vented and the liquid product recovered.

The liquid products, which were obtained with a 5.4 g weight gain, were analyzed by glc and Karl Fischer titration and the following product selectivity were obtained:

| | |
|---|---|
| methanol | 9 Wt % |
| ethanol | 29 Wt % |
| n-propanol | 6 Wt % |
| n-butanol | 3 Wt % |
| methyl Acetate | 13 Wt % |
| ethyl Acetate | 13 Wt % |
| n-propyl Acetate | 1 Wt % |
| n-butyl Acetate | 1 Wt % |
| water | 0.57 Wt % |

Catalyst productivity (based on weight gain)=5400 g/g-atm-Ru.

The ester products (C1~C4 acetate) were significantly increased and the ratio of methanol to ethanol is about 1.0:3.2 (9 Wt.% vs 29 Wt.%). The flexible product distributions by using samarium co-catalyst have been demonstrated.

What is claimed is:

1. A process for making alkanols which comprises reacting a mixture of CO and $H_2$ at a pressure of about 500 psig or greater and at a temperature of at least 150° C. in the presence of a catalyst system comprising a ruthenium-containing compound, a samarium-containing compound and a quaternary phosphonium salt, in the presence of an inert, oxygenated solvent.

2. The process of claim 1 wherein the process is conducted at a pressure of about 2000 psig to about 8000 psi.

3. The process of claim 1 wherein the process is conducted at a temperature of about 180° to about 250° C.

4. The process of claim 1 wherein the process is conducted with a ratio of CO to $H_2$ of 1:5 to 5:1.

5. The process of claim 1 wherein said quaternary salt is a tetraalkylphosphonium salt.

6. The process of claim 5 wherein said alkyl groups contain 1-6 carbon atoms.

7. The process of claim 1 wherein said quaternary salt is a mixed alkaryl phosphonium salt.

8. The process of claim 6 wherein said quaternary salt is tetrabutylphosphonium salt.

9. The process of claim 8 wherein said tetrabutylphosphonium salt is selected from the group consisting of tetrabutylphosphonium bromide, tetrabutylphosphonium chloride, tetrabutylphosphonium iodide, tetrabutylphosphonium acetate and tetrabutylphosphonium chromate.

10. The process of claim 9 wherein the said tetrabutylphosphonium salt is tetrabutylphosphonium bromide.

11. The process of claim 1 wherein the ruthenium-containing compound is selected from the group consisting of one or more oxides of ruthenium, ruthenium salts of an organic carboxylic acid, ruthenium complexes with carbonyl-containing ligands and ruthenium carbonyl or hydrocarbonyl containing ligands and ruthenium carbonyl or hydrocarbonyl derivatives.

12. The process of claim 11 wherein the said ruthenium-containing compound is selected from the group consisting of anhydrous ruthenium(IV) dioxide, ruthenium(IV) dioxide hydrate, ruthenium(VIII) tetraoxide, ruthenium acetate, ruthenium propionate, ruthenium(III) acetylacetonate and triruthenium dodecacarbonyl.

13. The process of claim 12 wherein said ruthenium-containing compound is ruthenium(IV) dioxide hydrated.

14. The process of claim 12 wherein said ruthenium-containing compound is ruthenium(III) acetylacetonate.

15. The process of claim 1 wherein the said samarium-containing compound is selected from the group consisting of samarium halides, samarium oxides, samarium hydrides, and samarium carboxylates.

16. The process of claim 15 wherein the said samarium compound is samarium chloride hydrate.

17. The process of claim 1 wherein the said solvent is selected from the group consisting of 1,3-dioxane, 1,4-dioxane, and diphenyl ether.

18. The process of claim 1 wherein the said solvent is 1,4-dioxane.

* * * * *

UNITED STATES PATENT AND TRADEMARK OFFICE
CERTIFICATE OF CORRECTION

PATENT NO. : 4,436,837

DATED : 3-13-84

INVENTOR(S) : Jiang-Jen Lin

It is certified that error appears in the above-identified patent and that said Letters Patent is hereby corrected as shown below:

Col. 8, line 40 delete "2000 psig" and substitute therefor --2000 psi--

Signed and Sealed this

Twenty-first Day of August 1984

[SEAL]

Attest:

GERALD J. MOSSINGHOFF

Attesting Officer

Commissioner of Patents and Trademarks